(12) United States Patent
Matsui

(10) Patent No.: US 9,457,120 B2
(45) Date of Patent: Oct. 4, 2016

(54) AIR PURIFIER

(71) Applicant: TOKUYAMA CORPORATION, Shunan-shi, Yamaguchi (JP)

(72) Inventor: Shingo Matsui, Shunan (JP)

(73) Assignee: TOKUYAMA CORPORATION, Shunan-shi, Yamaguchi (JP)

( * ) Notice: Subject to any disclaimer, the term of this patent is extended or adjusted under 35 U.S.C. 154(b) by 0 days.

(21) Appl. No.: 14/438,731

(22) PCT Filed: Nov. 13, 2013

(86) PCT No.: PCT/JP2013/080725
§ 371 (c)(1),
(2) Date: Apr. 27, 2015

(87) PCT Pub. No.: WO2014/077293
PCT Pub. Date: May 22, 2014

(65) Prior Publication Data
US 2015/0250913 A1 Sep. 10, 2015

(30) Foreign Application Priority Data

Nov. 19, 2012 (JP) ................................. 2012-252869

(51) Int. Cl.
*A61L 9/20* (2006.01)
*F24F 3/16* (2006.01)
*A61L 2/00* (2006.01)
*A61L 9/00* (2006.01)
*A61L 2/10* (2006.01)

(52) U.S. Cl.
CPC .. *A61L 9/20* (2013.01); *A61L 2/00* (2013.01); *A61L 2/10* (2013.01); *A61L 9/00* (2013.01); *F24F 3/16* (2013.01); *F24F 2003/1667* (2013.01)

(58) Field of Classification Search
USPC .......................... 250/453.11, 454.11, 455.11
See application file for complete search history.

(56) References Cited

U.S. PATENT DOCUMENTS

| 7,498,004 | B2 | 3/2009 | Saccomanno |
| 2003/0170151 | A1 | 9/2003 | Hunter et al. |
| 2013/0156649 | A1 | 6/2013 | Nakatani et al. |

FOREIGN PATENT DOCUMENTS

| JP | 11-063592 A | 3/1999 |
| JP | 2000-334448 A | 12/2000 |
| JP | 2001-009016 A | 1/2001 |

(Continued)

OTHER PUBLICATIONS

International Search Report dated Feb. 13, 2014; PCT/JP2013/080725.

*Primary Examiner* — Nicole Ippolito
*Assistant Examiner* — Hanway Chang
(74) *Attorney, Agent, or Firm* — Ladas & Parry LLP

(57) ABSTRACT

An air purifier including an air sterilizing unit, an air blowing unit arranged such that air flows in the air sterilizing unit; the air sterilizing unit comprising housing and an ultraviolet light emitting device which emits deep ultraviolet ray having wavelength of 200 to 350 nm; the housing comprising a sterilizing room; the sterilizing room comprising an air intake opening and an air outlet opening; and the ultraviolet light emitting device being arranged in the housing such that the deep ultraviolet ray is emitted toward inside of the sterilizing room, wherein (A) at least a part of an inner wall surface of the sterilizing room comprises an ultraviolet reflective material which may be covered with an ultraviolet ray transmitting material, and/or (B) one or more reflector plate is arranged in the sterilizing room.

13 Claims, 5 Drawing Sheets

(56) References Cited

FOREIGN PATENT DOCUMENTS

| | | |
|---|---|---|
| JP | 2005-006771 A | 1/2005 |
| JP | 2005-508228 A | 3/2005 |
| JP | 2008-104739 A | 5/2008 |
| JP | 2011-004832 A | 1/2011 |
| JP | 2012-205615 A | 10/2012 |
| KR | 100998473 B1 | 12/2010 |
| WO | 2008/105295 A1 | 9/2008 |
| WO | 2010/071814 A1 | 6/2010 |
| WO | 2012/023319 A1 | 2/2012 |

AIR PURIFIER

TECHNICAL FIELD

The present invention relates to a new air purifier.

BACKGROUND ART

Deep ultraviolet ray having a wavelength of 200 to 350 nm is known as having not only a function to act on nucleic acid which is protoplasm of bacteria to deprive them of proliferating ability, but also a function to destroy protoplasm to kill bacteria. An ultraviolet ray sterilizing apparatus which performs sterilization on bacteria by irradiating bacteria with ultraviolet ray having such functions are practically used. As a light source used in the ultraviolet ray sterilizing apparatus, a low pressure mercury lamp (so-called sterilization lamp) which emits light having a wavelength of 253.7 nm (resonance line of mercury) generated due to discharge of a low-pressure (approximately 0.1 Pa) mercury vapor is generally known. The sterilization lamp is widely used in various fields.

An air purifier having a sterilization ability by means of the sterilization lamp is also known. For example, as a stationary or wall-hanging type air purifier for purifying air in a living space such as a room, an air purifier including a body provided with inlet and outlet ports, the body including an air blowing unit including a centrifugal fan and a fan motor shaft-fastening the centrifugal fan, for forming an air passage in the body, wherein a filter and an ultraviolet ray sterilizing apparatus are provided in the order mentioned from an upstream side of the air passage, is known (see Patent Literatures 1 and 2). The above-described ultraviolet ray sterilizing apparatus is provided with a sterilization lamp (s) arranged on a center portion of a unit case made of a metal box, and with openings on the front side and back side of the unit case. The sterilizing apparatus is configured in such a way that air passes through the inside of the unit case, and sterilization is carried out by ultraviolet ray which irradiates the air which passes through the inside of the unit case. In the ultraviolet ray sterilizing apparatus used in a conventional air purifier as above, following measures are taken in order to prevent degradation of resin materials and adverse effects on human body that are caused by leakage of the ultraviolet ray. That is: firstly, in order to prevent ultraviolet ray from reflecting on the inner surface of the unit case, the inner surface is coated by a fluororesin coating material, or the inner surface itself is configured by an electrogalvanized steel sheet (SECC steel sheet) (Patent Literatures 1 and 2); secondly, in order to prevent leakage of ultraviolet ray from the opening, a cut and raised part is formed on the opening of the unit case (Patent Literature 1), or an ultraviolet ray-blocking member having a honey-combed shape, to the inner surface of which a ultraviolet ray absorbing coating material is applied, is attached (Patent Literature 2).

CITATION LIST

Patent Literatures

Patent Literature 1: JP H11-63592 A
Patent Literature 2: JP2005-6771 A

SUMMARY OF INVENTION

Technical Problem

The sterilization lamp, however, needs to be replaced relatively frequently since it has a short lifetime. In addition, in a case of breakage of the sterilization lamp, there is a fear that mercury is discharged outside.

It is considered that this kind of problems can be solved by employing a deep ultraviolet light emitting diode (hereinafter may be referred to as "deep ultraviolet LED") instead of the sterilization lamp. However, the deep ultraviolet LED has problems that the intensity of deep ultraviolet ray to be emitted therefrom (photon flux density or irradiance) is markedly lower than the intensity of deep ultraviolet ray to be emitted from the sterilization lamp, and that the irradiation range of ultraviolet ray is narrow, since it has a strong directivity of light to be emitted. Thus, in order to carry out a sufficient sterilization by means of the deep ultraviolet LED, huge numbers of deep ultraviolet LEDs need to be arranged on a plane surface to be used.

Solution to Problem

The inventor of the present invention focused on that air has a specifically high ultraviolet transmissivity compared to other substances. Then, the inventor has reached the idea that: if the deep ultraviolet ray emitted from the deep ultraviolet LED passes through an air layer which is to be sterilized more than once, by being reflected to change its light path, the deep ultraviolet ray can be effectively used, which results in reduction of the number of deep ultraviolet LEDs to be used. The present invention has been made based on the above idea.

The present invention is an air purifier including: an air sterilizing unit; an air blowing unit arranged such that air flows in the air sterilizing unit; the air sterilizing unit including a housing and an ultraviolet light emitting device which emits deep ultraviolet ray having wavelength of 200 to 350 nm; the housing comprising a sterilizing room; the sterilizing room including an air intake opening and an air outlet opening; and the ultraviolet light emitting device being arranged in the housing such that the deep ultraviolet ray is emitted toward inside of the sterilizing room, wherein (A) at least a part of an inner wall surface of the sterilizing room comprises an ultraviolet reflective material which may be covered with an ultraviolet ray transmitting material, and/or (B) one or more reflector plate is arranged in the sterilizing room wherein at least a part of the surface of the reflector plate comprises an ultraviolet reflective material which may be covered with an ultraviolet ray transmitting material; and the deep ultraviolet ray emitted from the ultraviolet light emitting device passes through air in the sterilizing room and thereafter further passes through the air in the sterilizing room once or more, by being reflected on the inner wall surface which includes the ultraviolet reflective material or on the surface of the reflector plate which includes the ultraviolet reflective material.

In view of efficiently using the deep ultraviolet ray, the ultraviolet reflective material is preferably chrome, platinum, rhodium, aluminum, barium, sulfate, magnesium oxide, calcium carbonate, or magnesium carbonate.

In the air purifier of the present invention, in view of safety, preferably the air sterilizing unit further includes an air-permeable and ultraviolet ray-blocking member so as to prevent leakage of the deep ultraviolet ray from the air intake opening and the air outlet opening.

The air purifier of the present invention, in order to carry out a higher-degree purification, preferably further includes a filter unit including a dust collecting filter, a deodorizing filter, or a complex filter which is a combination thereof, wherein the filter unit is attached in a removable manner on an upstream side of the air intake opening of the air sterilizing unit.

As the ultraviolet light emitting device, a deep ultraviolet LED can be preferably employed.

The ultraviolet reflective material is preferably a material having reflectance of no less than 40% against ultraviolet ray having wavelength of 265 nm.

As the ultraviolet ray-transmitting material, sapphire, quartz, or a polytetrafluoroethylene film is preferably employed.

As one preferable embodiment of the present invention, an embodiment wherein (a1) at least a part of the inner wall surface of the sterilizing room comprises the ultraviolet reflective material which may be covered with an ultraviolet transmitting material; and no less than 50% of an area of the inner wall surface of the sterilizing room directly or indirectly irradiated by the deep ultraviolet ray emitted from the ultraviolet light emitting device comprises the ultraviolet reflective material can be given.

It should be noted that, the expression "indirectly irradiated" by the deep ultraviolet ray means that being irradiated by the deep ultraviolet ray reflected more than once after being emitted from the ultraviolet light emitting device.

As one preferable embodiment of the present invention, an embodiment wherein (b1) the one or more reflector plate is arranged in the sterilizing room wherein at least a part of the surface of the reflector plate comprises the ultraviolet reflective material which may be covered with an ultraviolet transmitting material; and no less than 50% of an area of the surface of the reflector plate directly or indirectly irradiated by the deep ultraviolet ray emitted from the ultraviolet light emitting device comprises the ultraviolet reflective material can be given.

As one preferably embodiment of the present invention, an embodiment wherein (b2) the one or more reflector plate is arranged in the sterilizing room wherein at least a part of the surface of the reflector plate comprises the ultraviolet reflective material which may be covered with an ultraviolet transmitting material; and the one or more reflector plate is arranged such that a shortest flow path of air from flowing into the sterilizing room from the air intake opening to flowing out from the air outlet opening is made longer than in a case where the one or more reflector plate does not exist can be given.

As one preferable embodiment of the present invention, an embodiment wherein (b3) two or more said reflector plates are arranged in the sterilizing room wherein at least a part of the surface of the reflector plate comprises the ultraviolet reflective material which may be covered with an ultraviolet transmitting material; and the two or more reflector plates are arranged such that the surface comprises the ultraviolet reflective material of the two or more reflector plates are facing each other, such that deep ultraviolet ray reflected by one of the two or more reflector plate is further reflected by another one of the two or more reflector plates, can be given.

Advantageous Effect of Invention

The air purifier of the present invention uses an ultraviolet light emitting device such as a deep ultraviolet LED as the light source of ultraviolet ray and does not use a sterilization lamp (low-pressure mercury lamp), which is different from conventional air purifiers. Therefore, not only it is possible to save trouble and cost for maintenance, but also mercury is not discharged outside even when the apparatus is damaged. In addition, according to the air purifier of the present invention, it is possible to efficiently carry out sterilization of air, even though the intensity of the deep ultraviolet ray is low. Therefore, there is no need to use a huge amount of ultraviolet light emitting devices being arranged, therefore the apparatus can be downsized.

BRIEF DESCRIPTION OF DRAWINGS

FIG. 5 includes a schematic view of an air sterilizing unit in another embodiment of the air purifier of the present invention:

DESCRIPTION OF EMBODIMENTS

Similarly to a conventional air purifier having sterilization ability, the air purifier of the present invention is provided with a sterilizing apparatus in a flow path formed by an air blowing unit, to sterilize air flowing inside the sterilizing apparatus. Except that the apparatus having a new configuration is used as the sterilizing apparatus, other accessory devices (specifically, a dust collecting filter and a deodorizing filter to be optionally added in order to further improve purification function, and an air blowing unit, and the like) and arrangement thereof are not particularly different from those in the conventional air purifiers. In other words, in the air purifier of the present invention, it is needed that the above-described air sterilizing unit provided with a deep ultraviolet light emitting device is used instead of a conventional sterilizing apparatus provided with the sterilization lamp inside the unit case having openings. This is the greatest feature of the air purifier of the present invention. Therefore, first of all, the air sterilizing unit will be described in detail with the drawings.

Figure 1:
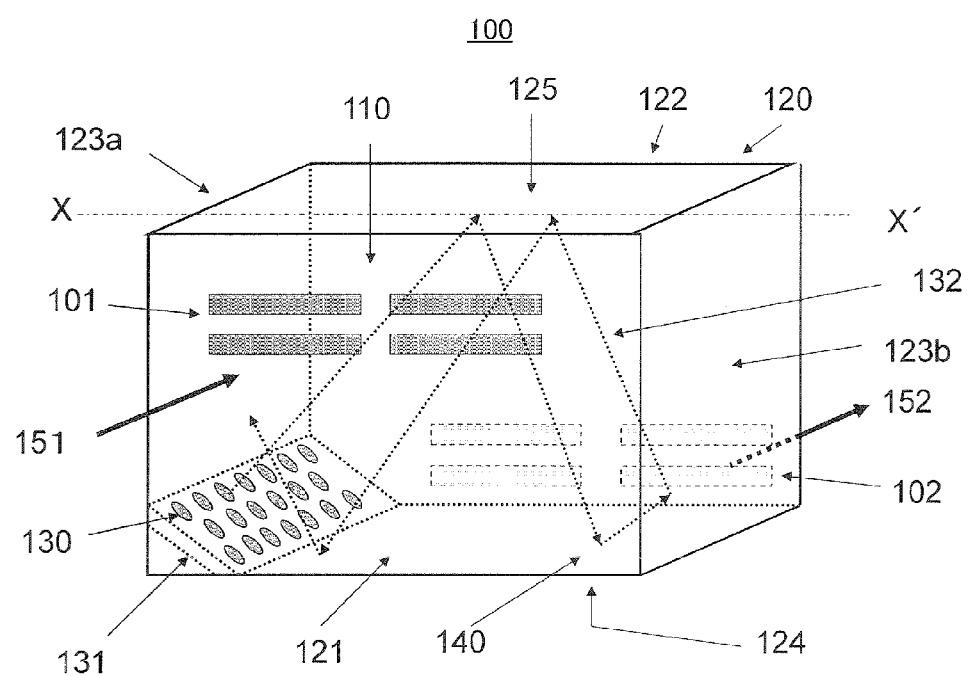
FIG. 1 is a schematic view (perspective view) of an air sterilizing unit in one embodiment of the air purifier of the present invention.

FIG. 1 is a schematic view (perspective view) of an air sterilizing unit 100 in one embodiment of the air purifier of the present invention. The air sterilizing unit 100 includes a housing 120 including a box body made of a metal or the like. On a front face 121 and back face 122 of the housing 120, an air intake opening 101 and an air outlet opening 102 are formed, respectively. It is preferable that each of these openings is provided with an air-permeable and ultraviolet ray-blocking member (not shown) so as to prevent leakage of the deep ultraviolet ray while allowing air flow.

The air-permeable and ultraviolet ray-blocking member is not particularly limited, as long as the member has a function to prevent leakage of deep ultraviolet ray emitted from an ultraviolet light emitting device 130 from the openings to the outside of the sterilizing room, when the deep ultraviolet ray directly goes to the openings or is reflected off an inner surface of the sterilizing room to be directed to the openings. For example, the cut and raised part, and the shielding plate to be attached inside the opening, which are shown in FIG. 17 of Patent Literature 1 (JP H11-63592 A), the ultraviolet ray-blocking member having a honeycombed shape as shown in FIG. 5 of Patent Literature 2 (JP2005-6771 A) and the like can be used as the air-permeable and ultraviolet-ray blocking member.

On a lower part of a side face 123a which is on a left side of the inside of the housing 120, a substrate 131 is removably fixed such that the substrate leans being inclined in a manner that a face of the substrate on which a plurality of ultraviolet light emitting devices 130 which emit deep ultraviolet ray having wavelength of 200 to 350 nm are arranged faces the direction of the top face of the housing. In this manner, the inner space of the housing 120 is separated into two rooms by the substrate 131. One of the two rooms which faces the face of the substrate 131 on which light emitting devices are arranged is a sterilizing room 110. In the sterilizing room 110, air entered from the air intake opening 101 is irradiated with the deep ultraviolet ray to be sterilized. The sterilized air is emitted from the air outlet opening 102. The other room which faces the opposite face from the face of the substrate 131 on which light emitting devices are arranged can be used as a space for storing wiring for supplying power required for lighting the ultraviolet light emitting device 130, from an external power supply (not shown), a safety device (not shown), and the like, or as a flow path to let air for cooling pass through.

Figure 2:
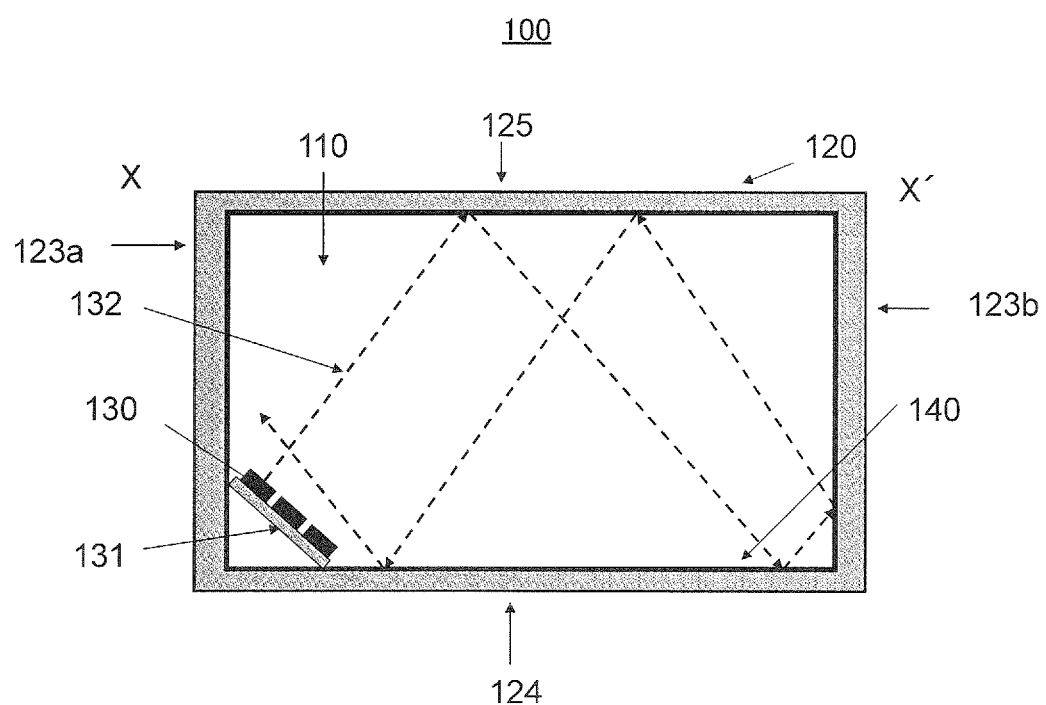
FIG. 2 is a longitudinal cross sectional view of the air sterilizing unit shown in FIG. 1.

As the ultraviolet light emitting device 130, an ultraviolet light emitting diode (deep ultraviolet LED) which emits deep ultraviolet ray having wavelength of 200 to 350 nm can be preferably used. It is desirable that the deep ultraviolet light emitting device is packaged or moduled, and arranged in a package having a structure such that light is emitted with strengthened directivity such as parallel light, for example a collimate lens. In a case where the directivity of emitted light is strong, the deep ultraviolet ray goes straight in a direction of a light axis 132. Thus the direction of the emitted light can be determined by direction of the face of the substrate 131 on which the light emitting devices are arranged. By arranging the substrate 131 perpendicular to the front face 121 having the opening 101 and back face 122 having the opening 102 of the housing as shown in FIG. 1, the emitted light travels parallel to these faces, and leakage of the deep ultraviolet ray from the openings 101 and 102 can be prevented. In a case where the directivity of emitted light (deep ultraviolet ray) is strong, the irradiation area of the emitted light is narrow. However, in the air sterilizing unit 100, as shown in FIGS. 1 and 2, the deep ultraviolet ray is reflected repeatedly on the opposite surfaces of the top face 125, bottom face 124, side faces 123a and 123b of the housing 120 (wall surfaces in the sterilizing room), to thereby pass through the air layer (layer of sterilization object) more than once. Therefore, it is possible to efficiently carry out sterilization even with the small number of ultraviolet light emitting devices.

In order to improve the reflection efficiency of the deep ultraviolet ray emitted from the ultraviolet light emitting device 130, in the air sterilizing unit to be used in the present invention, at least a part of an inner wall surface of the sterilizing room (specifically, preferably no less than 50% of an area of the inner wall surface of the sterilizing room directly or indirectly irradiated by the deep ultraviolet ray emitted from the ultraviolet light emitting device, more preferably no less than 70%, and most preferably no less than 90%) comprises an ultraviolet reflective material. Alternatively, the sterilizing room comprises a reflector plate wherein at least a part of the surface of the reflector plate comprises the ultraviolet reflective material. FIGS. 1 and 2 show the air sterilizing unit 100 in which whole inner surface of the sterilizing room comprises the ultraviolet reflective material, which is an inner surface 140. However, a part of the surface which the deep ultraviolet ray does not hit does not necessarily need to comprise the ultraviolet reflective material. Here, the ultraviolet reflective material means a material having reflectance of no less than 40%, preferably no less than 60%, and most preferably no less than 70%, against deep ultraviolet ray, especially ultraviolet ray having wavelength of 250 to 270 nm, especially 265 nm. Examples of the ultraviolet reflective material which can be preferably used in the present invention include chrome (ultraviolet reflectance: approx. 50%), platinum (ultraviolet reflectance: approx. 50%), rhodium (ultraviolet reflectance: approx. 65%), barium sulfate (ultraviolet reflectance: approx. 95%), magnesium carbonate (ultraviolet reflectance: approx. 75%), calcium carbonate (ultraviolet reflectance: approx. 75%), magnesium oxide (ultraviolet reflectance: approx. 90%), and aluminum (ultraviolet reflectance: approx. 90%). Among them, rhodium, platinum, or aluminum is especially preferable as the ultraviolet reflective material since it is possible to make the surface have higher reflectance, by means of a surface treatment such as plating and vapor deposition. In a case where a metal material is employed for the ultraviolet reflective material, it is preferable that the surface of the material is covered with an ultraviolet ray-transmitting material such as sapphire, quartz, or a polytetrafluoroethylene film, in view of preventing degradation of the reflectance due to oxidation of or scratch on the surface.

In view of easy maintenance and the like, is preferable that a deep ultraviolet sensor having sensitivity to deep ultraviolet ray, such as alight receiving element, is arranged inside the sterilizing room of the air sterilizing unit 100, so that it is possible to check the working state of the ultraviolet light emitting device 130 from outside.

The air sterilizing unit 100 shown in FIGS. 1 and 2 is described as above. However, the reflection of the ultraviolet ray can be made not only by means of the inner surface of the sterilizing room, but also by means of a reflector plate arranged in the sterilizing room. The reflector plate also has a function of a plate for changing air flow for elongating air flow path in the sterilizing room. By arranging the reflector plate in the sterilizing room, it becomes possible to certainly irradiate the air with ultraviolet ray. Therefore, it is preferable that the reflector plate is arranged in the sterilizing room. It is preferable that no less than 50% of an area of the surface of the reflector plate directly or indirectly irradiated by the deep ultraviolet ray emitted from the ultraviolet light emitting device comprises the ultraviolet reflective material. The rate of the area configured by the ultraviolet reflective material to the area to be directly or indirectly irradiated by the deep ultraviolet ray in the surface of the reflector plate is more preferably no less than 70%, and most preferably no less than 90%. Hereinafter, with reference to FIG. 4, an air sterilizing unit provided with the reflector plate is described.

Figure 4:
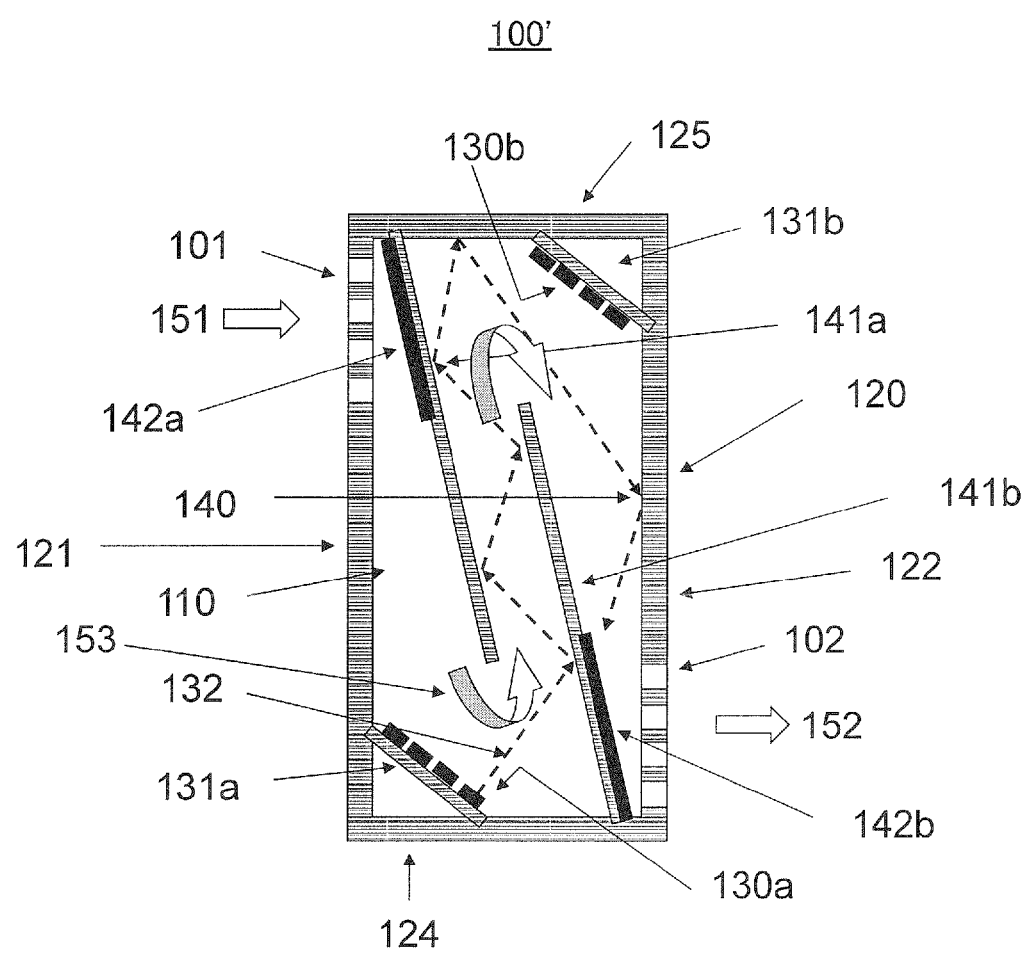
FIG. 4 is a schematic view (longitudinal cross sectional view) of an air sterilizing unit in another embodiment of the air purifier of the present invention.

FIG. 4 is a cross sectional view of an air sterilizing unit 100' provided with the reflector plate (seen in a direction of a side face of the housing). In the air sterilizing unit 100', a substrate 131a on which ultraviolet light emitting devices 130a are arranged is arranged between the front face 121 and bottom face 124 of the housing, such that the substrate leans against the front face, and the substrate 131b on which ultraviolet light emitting devices 130b are arranged is arranged between the back face 122 and top face 125 of the housing. Whereby, the sterilizing room is formed. In the sterilizing room 110, reflector plates 141a and 141b are fixed to the top and bottom faces of the housing 120, respectively, so as to be inclined at a predetermined distance. The reflector plates divide the sterilizing room into three spaces. Each reflector plate is a rectangular plate body, whose long side has a length same as the width of the sterilizing room (long side of the front face) and short side has a length shorter than the height of the sterilizing room (short side of the front face). Therefore, when the two reflector plates are arranged as shown in FIG. 4, the sterilizing room is divided into: a space between the front face 121 and the reflector plate 141a (may be referred to as "space 1"); a space between the two reflector plates (may be referred to as "space 2"); and a space between the reflector plate 141b and the back face 122 (may be referred to as "space 3"). Then, as shown by an arrow 153 in FIG. 4, the air in the sterilizing room flows downwardly in the space 1 from the air intake opening 101 provided to an upper part of the sterilizing room, thereafter inverts its flow and flows upwardly in the space 2, then inverts its flow again and flows in the space 3 toward the air outlet opening 102 provided to a lower part of the sterilizing room.

Since the reflector plates are arranged and the space is divided into three spaces which communicate with one another, the thickness of the air layer through which the deep ultraviolet ray passes becomes thin, and the air entered in the sterilizing room definitely flows in the spaces 1, 2 and 3 without shortcutting its flow pass. In the air sterilizing room 100', since the inner surface of the sterilizing room consists of the ultraviolet reflective material, the air which moves in each space is irradiated with ultraviolet ray more than once in each space. That is, by arranging the reflector plate, the air layer through which the deep ultraviolet passes becomes thin, and the air flow path is elongated then the number of times the air is irradiated with the ultraviolet ray increases. Therefore, it becomes possible to carry out sterilization more certainly. In addition, by the ultraviolet absorbing material included on a part of the surface of the reflector plates which part faces the air intake opening 101 and on a part of the surface of the reflector plates which part faces the air outlet opening 102, reflection of light toward the openings can be prevented, and leakage of ultraviolet ray from the openings can be prevented more certainly.

Other than the air sterilizing unit, the air purifier of the present invention needs to include at least an air blowing unit. In addition to these, if necessary, the air purifier can have a body of the purifier, a filter, a power supply device, a control unit, a control panel, a heat exchange device for temperature control and the like (hereinafter may be referred to as "optional devices" or "optional members"), as well as a conventional air purifier. As described above, the air purifier of the present invention is not particularly different from a conventional air purifier, except that the air sterilizing unit is used as the sterilizing apparatus. Therefore, an air blowing unit used in a conventional air purifier can be used without particular limitations as the air blowing unit required for forming the flow path. For example, the air blowing unit including a cylindrical centrifugal fan with a lot of blades arranged on its periphery and a fan motor shaft-fastening the centrifugal fan, as disclosed in the above Patent Literature 1 or 2 can be used.

Figure 3:
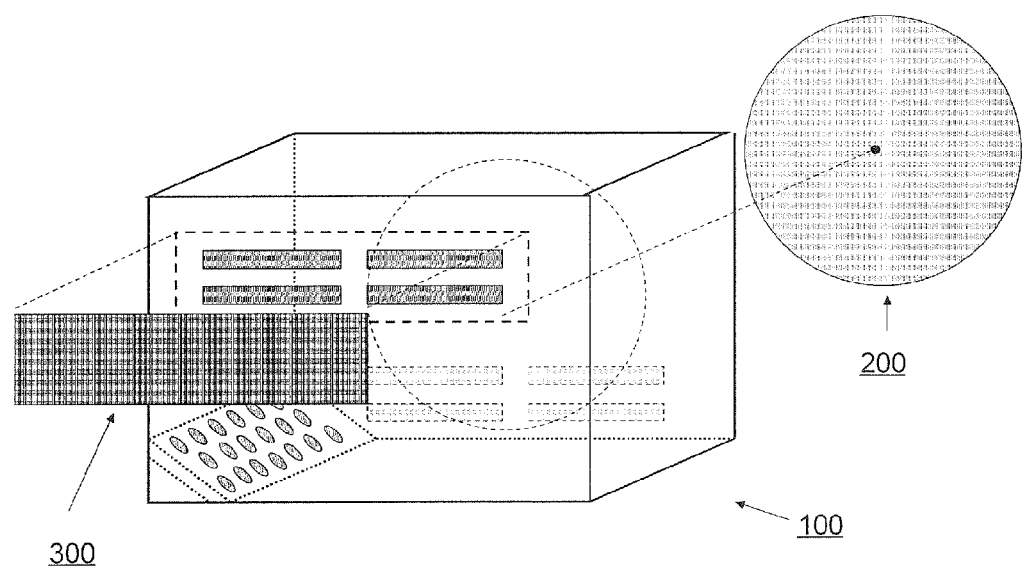
FIG. 3 is a schematic view to explain the arrangement of each device and member in the air purifier of the present invention provided with the air sterilizing unit shown in FIG. 1.

In addition, in the air purifier of the present invention, optional devices or members same as or similar to the devices or members used in a conventional air purifier can be adequately added. For example, it is preferable to further improve purification function by adding various kinds of filter such as a dust collecting filter and a deodorizing filter, an electric dust collector and the like, as well as a conventional air purifier. For example, in Patent Literature 2, a filter unit in which a prefilter, a dust collecting filter and a deodorizing filter are integrated in a manner to be layered in the order mentioned is used. The air purifier of the present invention can also include a similar filter unit. Further, in the air purifier of the present invention, it is preferable that the air sterilizing unit 100 and an air blowing unit 200 that form the sterilizing apparatus, and a filter unit 300 and the like used if necessary, are adequately arranged in the housing to be a body of the purifier as well as a conventional air purifier, for example "a main body configured by a front panel provided with a display on its front and intake openings on its both side faces, and a back panel provided with an outlet opening formed by a plurality of sashes on its top face" as disclosed in Patent Literature 2. FIG. 3 shows an arrangement relation of the air sterilizing unit 100, air blowing unit 200 and filter unit 300 of the present invention.

Figure 5A:
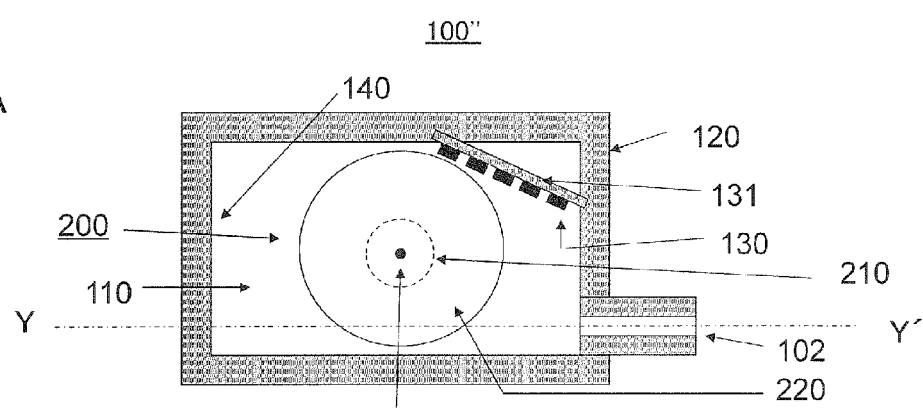
FIG. 5A is a longitudinal cross sectional view seen from the front surface side.
Figure 5B:
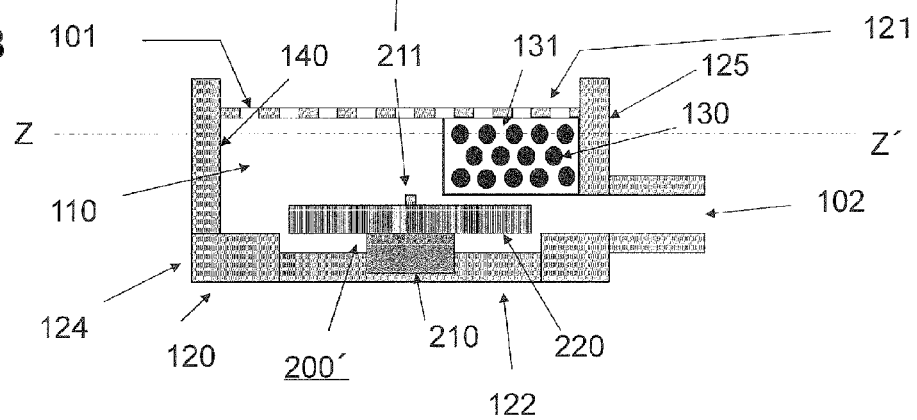
FIG. 5B is a longitudinal cross sectional view seen from a side face side.

A stationary or wall-hanging type air purifier for purifying air in a room and the like is explained as above. However, the air purifier of the present invention is not limited to these embodiments. For example, by having the structure shown in FIGS. 5A and 5B, the air purifier can be used as a supplying unit of purified air in a respiration protector with electric fan. FIGS. 5A and 5B show an air sterilizing unit 100" in which an air blowing unit is arranged in the sterilizing room, in order for the sterilizing unit 100" to be downsized and used portably. The air blowing unit can be arranged inside the sterilizing room as above. The air sterilizing unit 100" has a flat shape and mostly used in a state of standing. Therefore, the right side on the sheet of paper of FIG. 5 is the upper side of the sterilizing unit 100" in use. FIG. 5A is a longitudinal cross sectional view seen from the front side in use (taken along the line Z-Z'), and FIG. 5B is a longitudinal cross sectional view seen from a side face side in use (taken along the line Y-Y'). By removably attaching a filter unit (not shown) at a recess formed outside the front face 121, and having a structure in which the ultraviolet light emitting device 130 and a fan motor 210 of the air blowing unit 200' are powered by a battery (not shown), it is possible to make the air sterilizing unit 100" portable.

DESCRIPTION OF REFERENCE NUMERALS 100,100',100" air sterilizing unit
101 air intake opening
102 air outlet opening
110 sterilizing room
120 housing
121 front face of housing
122 back face of housing
123a, 123b side face of housing
124 bottom face of housing
125 top face of housing
130, 130a, 130b ultraviolet light emitting device
131, 131a, 131b substrate
132 light axis (traveling direction) of deep ultraviolet luminous flux emitted from ultraviolet light emitting device
140 inner surface including ultraviolet reflective material
141a, 141b reflector plate wherein at least a part of surface consists of ultraviolet reflective material
142a, 142b surface consists of ultraviolet absorbing material
151 air flow to be taken from air intake opening
152 air flow emitted from air outlet opening
153 air flow in sterilizing room
200,200' air blowing unit 210 fan motor
211 rotation axis
220 centrifugal fan
300 filter unit

The invention claimed is:
1. An air purifier comprising:
an air sterilizing unit;
an air blowing unit arranged such that air flows in the air sterilizing unit;
the air sterilizing unit comprising:
a housing comprising a box body;
a substrate removably fixed in the housing; and
a plurality of ultraviolet light emitting diode arranged on the substrate and emitting deep ultraviolet ray having wavelength of 200 to 350 nm;
the housing comprising a sterilizing room;
the sterilizing room being an inner space of the housing and facing a face of the substrate on which light emitting devices are arranged, and comprising an air intake opening and an air outlet opening; and
the ultraviolet light emitting diode being arranged in a package having a structure such that light is emitted with strengthened directivity, and being arranged in the housing such that the deep ultraviolet ray is emitted toward inside of the sterilizing room,
wherein (A) at least a part of an inner wall surface of the sterilizing room comprises an ultraviolet reflective material which may be covered with an ultraviolet ray transmitting material, and/or (B) one or more reflector plate which is a plate body is arranged and fixed in the sterilizing room wherein at least a part of the surface of the reflector plate comprises the ultraviolet reflective material; and
the deep ultraviolet ray emitted from the ultraviolet light emitting diode passes through air in the sterilizing room and thereafter further passes through the air in the sterilizing room once or more, by being reflected on the inner wall surface which comprises the ultraviolet reflective material or on the surface of the reflector plate which comprises the ultraviolet reflective material.
2. The air purifier according to claim 1,
wherein the ultraviolet reflective material is chrome, platinum, rhodium, aluminum, barium sulfate, magnesium oxide, calcium carbonate, or magnesium carbonate.
3. The air purifier according to claim 1,
wherein the air sterilizing unit further comprises an air-permeable and ultraviolet ray-blocking member so as to prevent leakage of the deep ultraviolet ray from the air intake opening and the air outlet opening.
4. The air purifier according to claim 1, further comprising:
a filter unit comprising a dust collecting filter, a deodorizing filter, or a complex filter which is a combination thereof,
wherein the filter unit is attached in a removable manner on an upstream side of the air intake opening of the air sterilizing unit.
5. The air purifier according to claim 1,
wherein the ultraviolet reflective material is a material having reflectance of no less than 40% against ultraviolet ray having wavelength of 265 nm.
6. The air purifier according to claim 1,
wherein the ultraviolet ray-transmitting material is sapphire, quartz, or a polytetrafluoroethylene film.
7. The air purifier according to claim 1,
wherein (a1) at least a part of the inner wall surface of the sterilizing room comprises the ultraviolet reflective material; and
no less than 50% of an area of the inner wall surface of the sterilizing room directly or indirectly irradiated by the deep ultraviolet ray emitted from the ultraviolet light emitting diode comprises the ultraviolet reflective material.
8. The air purifier according to claim 1,
wherein (b1) the one or more reflector plate is arranged in the sterilizing room wherein at least a part of the surface of the reflector plate comprises the ultraviolet reflective material; and
no less than 50% of an area of the surface of the reflector plate directly or indirectly irradiated by the deep ultraviolet ray emitted from the ultraviolet light emitting diode comprises the ultraviolet reflective material.
9. The air purifier according to claim 1,
wherein (b2) the one or more reflector plate is arranged in the sterilizing room wherein at least a part of the surface of the reflector plate comprises the ultraviolet reflective material; and
the one or more reflector plate is arranged such that a shortest flow path of air from flowing into the sterilizing room from the air intake opening to flowing out from the air outlet opening is made longer than in a case where the one or more reflector plate does not exist.
10. The air purifier according to claim 1,
wherein (b3) two or more said reflector plates are arranged in the sterilizing room wherein at least a part of the surface of the reflector plate comprises the ultraviolet reflective material; and
the two or more reflector plates are arranged such that the surfaces comprising the ultraviolet reflective material of the two or more reflector plates are facing each other, such that deep ultraviolet ray reflected by a first reflector plate is further reflected by a second reflector plate.
11. The air purifier according to claim 1,
wherein the substrate is arranged in the housing such that leakage of the deep ultraviolet ray from the air intake opening and the air outlet opening is prevented by the direction of the emitted light determined by direction of the face of the substrate on which light emitting devices are arranged.
12. The air purifier according to claim 11,
wherein the housing comprises a front face, a back face, a top face, a bottom face, and side faces;
the air intake opening is formed in the front face;
the air outlet opening is formed in the back face; and
the substrate is arranged perpendicular to the front face and the back face such that leakage of deep ultraviolet ray from the air intake opening and the air outlet opening is prevented.
13. The air purifier according to claim 11,
wherein the housing comprises a front face, a back face, a top face, a bottom face, and side faces;
the air intake opening is formed in the front face;
the air outlet opening is formed in the back face;
the substrate is arranged between the front face and the bottom face such that the substrate leans against the front face;
two said reflector plates are arranged and fixed inclined in the sterilizing room at a predetermined distance, on the top face of the housing and on the bottom face of the housing respectively, such that air flow path in the sterilizing room is elongated; and leakage of deep ultraviolet ray from the air intake opening and the air outlet opening is prevented by an ultraviolet absorbing material comprised on a part of the surface of the reflector plates which part faces the air intake opening and on a part of the surface of the reflector plates which part faces the air outlet opening.

* * * * *